United States Patent
Clarke et al.

(10) Patent No.: US 9,922,574 B2
(45) Date of Patent: Mar. 20, 2018

(54) METHOD AND APPARATUS FOR TEACHING UTILIZING MOVING WALKWAYS

(71) Applicants: James Clarke, Washington, DC (US); Chiedo Ohanyerenwa, Washington, DC (US)

(72) Inventors: James Clarke, Washington, DC (US); Chiedo Ohanyerenwa, Washington, DC (US)

(73) Assignee: Forward Entertainment & Technology, LLC, Washington, DC (US)

(*) Notice: Subject to any disclaimer, the term of this patent is extended or adjusted under 35 U.S.C. 154(b) by 71 days.

(21) Appl. No.: 14/217,512

(22) Filed: Mar. 18, 2014

(65) Prior Publication Data

US 2014/0272848 A1   Sep. 18, 2014

Related U.S. Application Data

(60) Provisional application No. 61/786,840, filed on Mar. 15, 2013.

(51) Int. Cl.
| | |
|---|---|
| *G09B 19/00* | (2006.01) |
| *G09B 5/00* | (2006.01) |
| *G02F 1/133* | (2006.01) |
| *G02F 1/1335* | (2006.01) |
| *G02F 1/1333* | (2006.01) |

(52) U.S. Cl.
CPC ............ *G09B 5/00* (2013.01); *G02F 1/133* (2013.01); *G02F 1/13336* (2013.01); *G02F 1/133385* (2013.01); *G02F 1/133526* (2013.01); *G02F 1/133603* (2013.01)

(58) Field of Classification Search
None
See application file for complete search history.

(56) References Cited

U.S. PATENT DOCUMENTS

| | | | | |
|---|---|---|---|---|
| 5,591,104 A * | 1/1997 | Andrus | ............... | A61B 5/6887 434/247 |
| 5,984,839 A * | 11/1999 | Corkum | ............ | A63B 71/0622 482/4 |
| 6,458,060 B1 * | 10/2002 | Watterson | .......... | A63B 24/0084 482/4 |
| 6,902,513 B1 * | 6/2005 | McClure | ............ | A63B 24/0006 482/4 |
| 7,044,891 B1 * | 5/2006 | Rivera | ............... | A63B 21/0053 482/1 |

(Continued)

*Primary Examiner* — Sunit Pandya
(74) *Attorney, Agent, or Firm* — Forward Entertainment & Technology, LLC; James Lowell Ramsey Clarke; Chiedo Raymond Ohanyerenwa

(57) ABSTRACT

A room or area designed to facilitate a plurality of users moving while they learn, work, or participate in a simulation. sensor relays aid this process by sending and receiving user information to a central hub, a movement device, one another or any combination of the three, in order to safely benefit the users coordination, exercise, or concentration while multitasking, according to their own user defined set points, a set of default set points, or set points determined by an external observer. This room or area may be further enhanced in applications where a treadmill or moving walkway is present.

20 Claims, 14 Drawing Sheets

(56) References Cited

U.S. PATENT DOCUMENTS

| | | | | |
|---|---|---|---|---|
| 8,939,831 B2* | 1/2015 | Dugan | .................. | A63F 13/212 |
| | | | | 463/31 |
| 8,992,383 B2* | 3/2015 | Bilang | .................... | A63B 22/02 |
| | | | | 482/1 |
| 9,367,668 B2* | 6/2016 | Flynt | .................. | A63B 24/0087 |
| 2003/0017913 A1* | 1/2003 | Stewart | .................. | A63B 22/00 |
| | | | | 482/8 |
| 2006/0205566 A1* | 9/2006 | Watterson | .......... | A63B 24/0084 |
| | | | | 482/8 |
| 2012/0237911 A1* | 9/2012 | Watterson | .......... | A63B 24/0087 |
| | | | | 434/247 |
| 2013/0288223 A1* | 10/2013 | Watterson | .............. | G09B 19/00 |
| | | | | 434/428 |
| 2014/0190789 A1* | 7/2014 | Clarke | .................... | B66B 3/002 |
| | | | | 198/321 |

* cited by examiner

METHOD AND APPARATUS FOR TEACHING UTILIZING MOVING WALKWAYS

CROSS-REFERENCE TO RELATED APPLICATION

This application claims the benefit of U.S. Provisional Application No. 61/786,840 filed Mar. 15, 2013. The entire disclosure of U.S. Provisional Application No. 61/786,840 is incorporated herein by reference.

TECHNICAL FIELD

The general field of the disclosure herein relates to methods, systems, or apparatuses involving rooms with interactive moving walkways, treadmills, or other moving devices. More specifically these moving devices may act in response to the commands of a user or an observer, in unison, or independently. The systems, methods and apparatuses of the disclosure involve a room wherein the user or a plurality of users move on a moving walkway or a plurality of moving walkways, while simultaneously processing (via: learning; creating through typing, moving, or talking; or being entertained) and receiving feedback or assistance related to that movement, processing, or any combination thereof.

BACKGROUND

Studies related to multitasking have shown that people typically process one task less efficiently when coupled with other tasks (see, e.g., "Cognitive Control in Media Multitaskers" by Ophir and Wagner, Proceedings of the National Academy of Sciences of the United States of America, 2009). Ophir and Wagner found that media related multitasking was distinct from normal multitasking, and caused users switching between activities to perform worse than during normal multitasking. Terms such as cognitive distraction, distracted driving, distracted walking, visual distraction, and manual distraction describe the ways in which people lose focus or the ability to provide a timely response to a situation to which they would otherwise be able to respond, due to an additional task.

Conversely, studies have shown that movement can stimulate the functionality of the brain, (see, e.g., "Exercise and the brain: something to chew on" by Van Praag, National Institute of Health, Trends in Neuroscience, 2009). Van Praag finds that optimal maintenance and brain health may depend on exercise and intake of natural products. Furthermore feedback and assistance while multitasking can be used to stimulate better coordination of movement and any additional tasks. The benefits of movement related to coordination, exercise, and physiotherapy are numerous, including stimulated muscle memory and reflexes due to repetitive movements involving hand-eye coordination, improved health due to weight loss or lowered blood pressure, increased longevity, restoration of function and movement, and the treatment, healing and prevention of injuries or disabilities. Studies show that increasing numbers of people are living sedentary lifestyles (See e.g. "Amount of Time Spent in Sedentary Behaviors in the United States, 2003-2004" by Charles E. Matthews et. al., American Journal of Epidemiology, 2008). In his study, Matthews found evidence that most Americans, both male and female over the ages of 6-11 now spend over 50% of their time in sedentary behaviors. This is at least partially related to the drawbacks of the information age, in which many people learn, create or conduct business, or are entertained all from a stationary position while observing monitors on their televisions and computers.

While inventions exist that allow movement while creating such as the laptop computer, movement while reading or learning such as tablet processors, or movement while being entertained such as virtual reality headsets like the Vuzix wrap 230 eyewear product, none of these devices are designed specifically for use while moving, and none of them are designed to provide feedback to the user or assistance to the user specifically related to that movement. A system method or apparatus specifically designed to allow the user to process, by learning, creating, or being entertained; while moving through coordination, exercise, or physiotherapy; and that aids the user in providing feedback or assistance related to that movement, processing, or any combination thereof; has the potential of being a boon to society.

Furthermore studies have shown that the average human attention span fell from 12 minutes in 1998 to just 5 minutes in 2008 (See e.g. "Stress of Modern Life Cuts Attention Spans to Five Minutes" by Moore, The Telegraph, Nov. 8, 2008) Moore cites a Lloyds TSB Insurance Study which also found that adults over 50 were able to concentrate for younger periods of time than younger people, suggesting that our media heavy and increasingly sedentary lifestyles may be taking its toll on younger generations. If these trends progress they could have potentially devastating effects on the future of our society. Conversely studies have shown that people are capable of longer attention spans when they are doing something they find enjoyable or intrinsically motivating. (See e.g. Dukette, Cornish *The Essential 20: Twenty Components of an Excellent Health Care Team*. RoseDog Books. 2009) Dukette and Cornish's study shows that attention spans for sustained attention to a freely chosen task range from about 5 minutes in a two-year-old child, to a maximum of 20 minutes in adults. An invention, that ergonomically incorporates the brains processing of external media with movement and exercise, could be revolutionary in a classroom, simulation, or work setting. An area devoted to such movement could be used as an energy efficient training facility, exercise and learning room, or meditation and rehabilitation area.

SUMMARY OF THE INVENTION

The disclosure herein is related to rooms involving one or more moving devices and may further involve a plurality of users moving while receiving sensory information. Sensory information is defined as audio, visual, and tactile information, which may also be received in the form of feedback to the user, in response to her movements or lack thereof. This room may have several embodiments including but not limited to: a room containing a single treadmill, spanning the length of the room, wherein the user may send a signal to direct the starting or stopping of said treadmill; an area containing a single moving walkway spanning the width of the room, with a raised floor above said moving walkway with holes in the floor so that users entering the holes may access the moving walkway; a room with a plurality of moving devices which the users may utilize while conducting tasks such as learning, working, creating something on a computer device, or being engaged in a simulation all while moving and outputting sensory information related to those tasks, their movement, or both to one or more devices.

Sensory information collected by those devices may include but is not limited to any audio, visual, or tactile information, which may relate to the users actions or inactions in performing those tasks or in moving. That information may be sent from those devices, herein referred to as sensor relays, to one or more other devices, including but not limited to other sensor relays, computer processors or movement devices. The sensor relay may instead output the information to an output device which converts the information into a form that the user or an observer understands. If the information is received by a computer processor, the computer processor may analyze the information against a set of predetermined set points before sending signals to other devices including but not limited to output devices and movement devices. Movement devices may include any device designed to facilitate movement, including but not limited to treadmills or moving platforms, bicycles, elliptical machines, cable row machines, automatically adjustable weight devices. When receiving a signal from the computer processor, signal relay, or a user or observer who has received feedback regarding the user's sensory information, the movement device may respond accordingly.

This disclosure also describes a method for using the room's moving devices to aid in teaching students. This may be accomplished in a variety of ways including but not limited to classrooms with walkways under stationary platforms to allow a teacher to present a lecture to students while the students are in motion on a moving walkway or classrooms where students learn while on various treadmills and the teacher can communicate with them wirelessly. Among the objectives of this disclosure is to provide a room or area which ergonomically incorporates the user's processing and receiving information and feedback while moving. For instance a room containing an ellipsoidal shaped treadmill interface may allow the user to move in a pattern that allows them to take advantage of centripetal acceleration efficiently, while receiving sensory feedback without the distraction of lagging and falling off of a standard treadmill. The network of treadmills described could be used for conservation of energy for electrical efficiency purposes so that the same energy source powering the network can conserve energy as it powers the sensory interface component.

It is envisioned that this disclosure will be used for a plurality of users exercising while effectively learning through receiving audio visual information without distractions from multitasking, playing interactive games while moving which may interface with the users movement, listening to or creating audio recordings while exercising effectively, or moving in an immersive technology environment while wearing a translucent headset which displays an image or video on a large monitor visible to all users.

While the preferred embodiments of the invention are shown in the accompanying drawings, it is still to be understood that said embodiments are susceptible to modification and alteration while still maintaining the spirit of my invention.

BRIEF DESCRIPTION OF THE DRAWINGS

Referring to the drawings.

DETAILED DESCRIPTION

Figure 1:
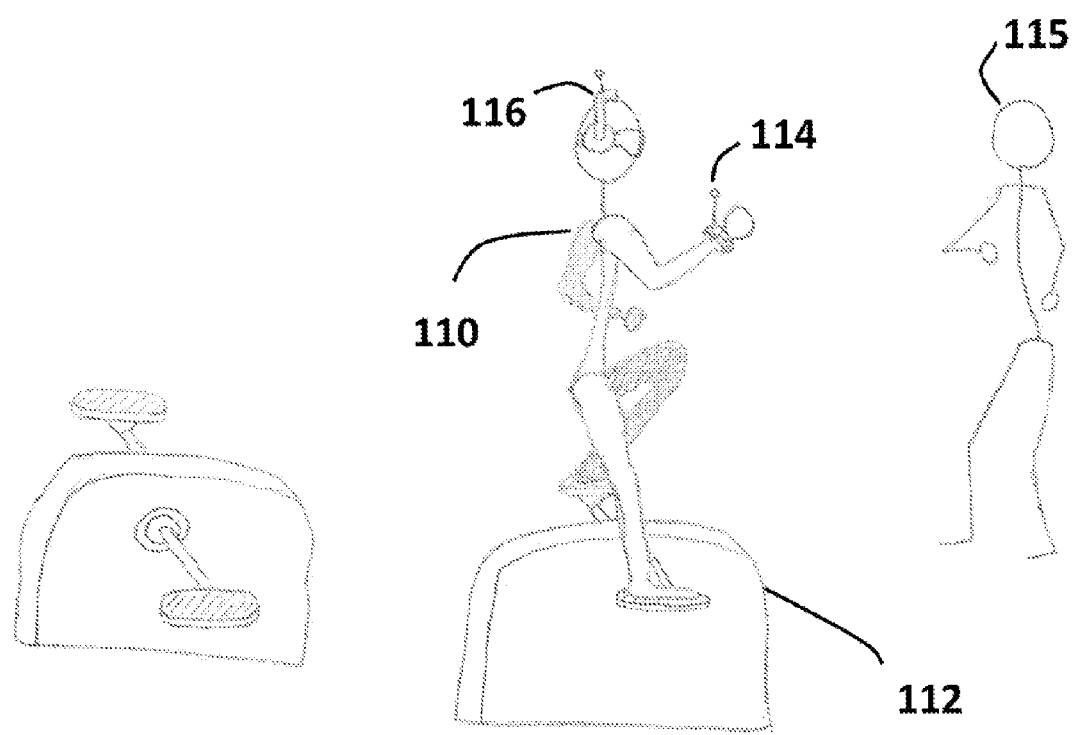
FIG. 1 is an illustration of a room with a plurality of movement devices, wherein a user receives sensory feedback related to his movement and performance through an output device.
Figure 2:
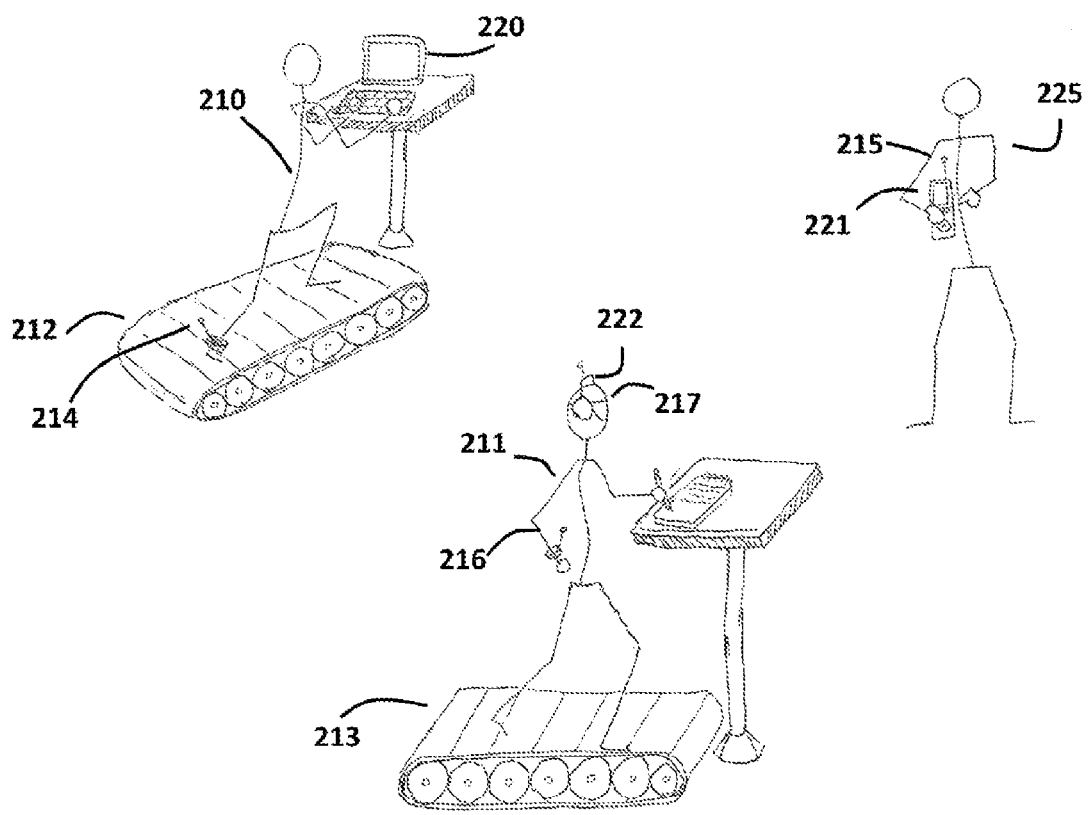
FIG. 2 illustrates a room with a plurality of moving devices and a plurality of users, whose performance related activity is transmitted from sensor relays to an observers output device.
Figure 3:
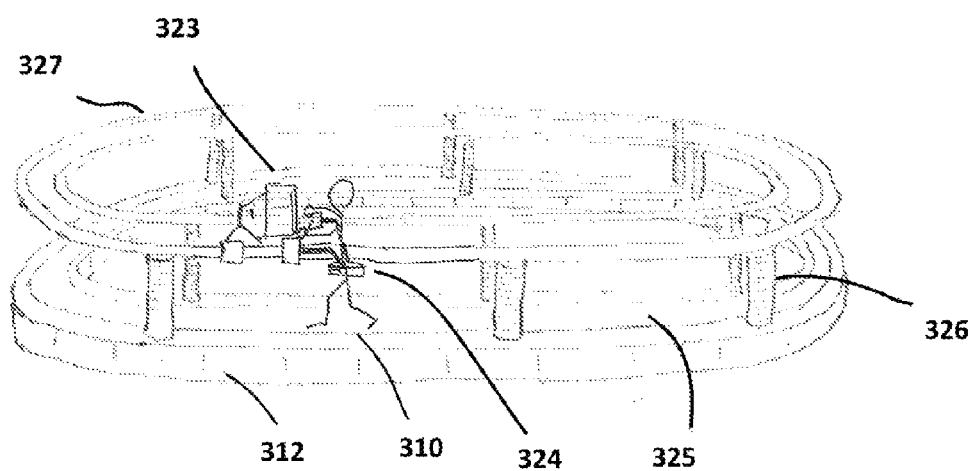
FIG. 3 illustrates a room with a moving device comprising a work station which moves in response to the user's movement.
Figure 4:
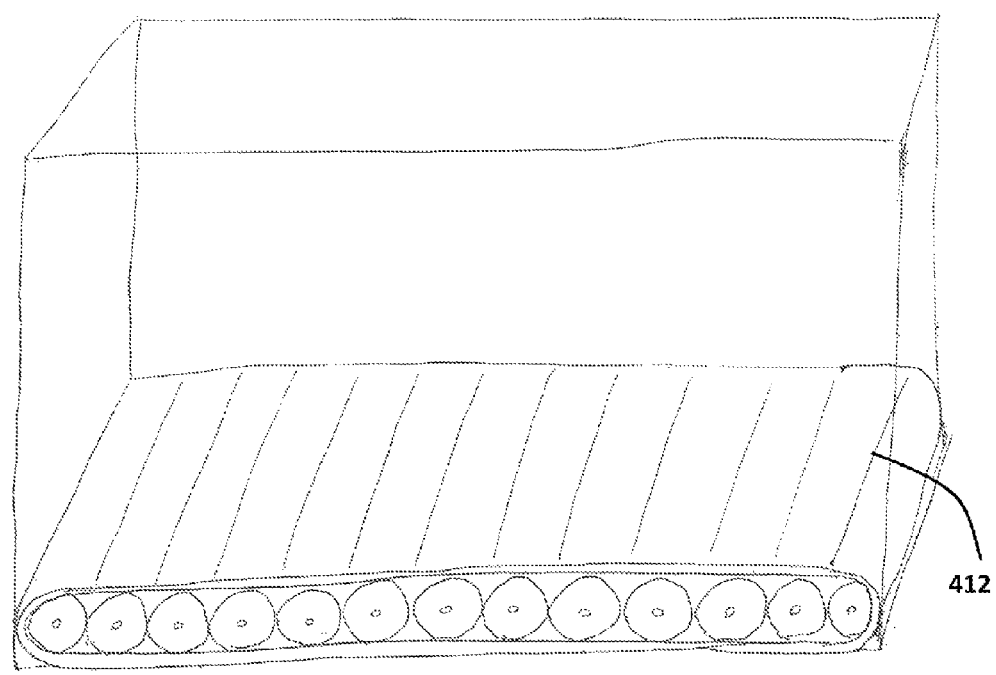
FIG. 4 illustrates a room wherein the entire floor is a moving walkway.
Figure 5:
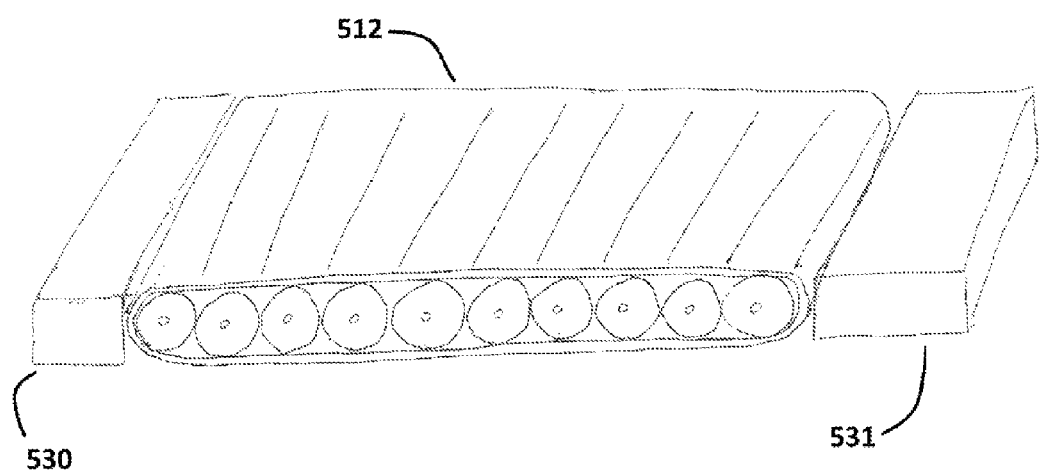
FIG. 5 illustrates a room with a moving walkway spanning the width of the room.
Figure 6:
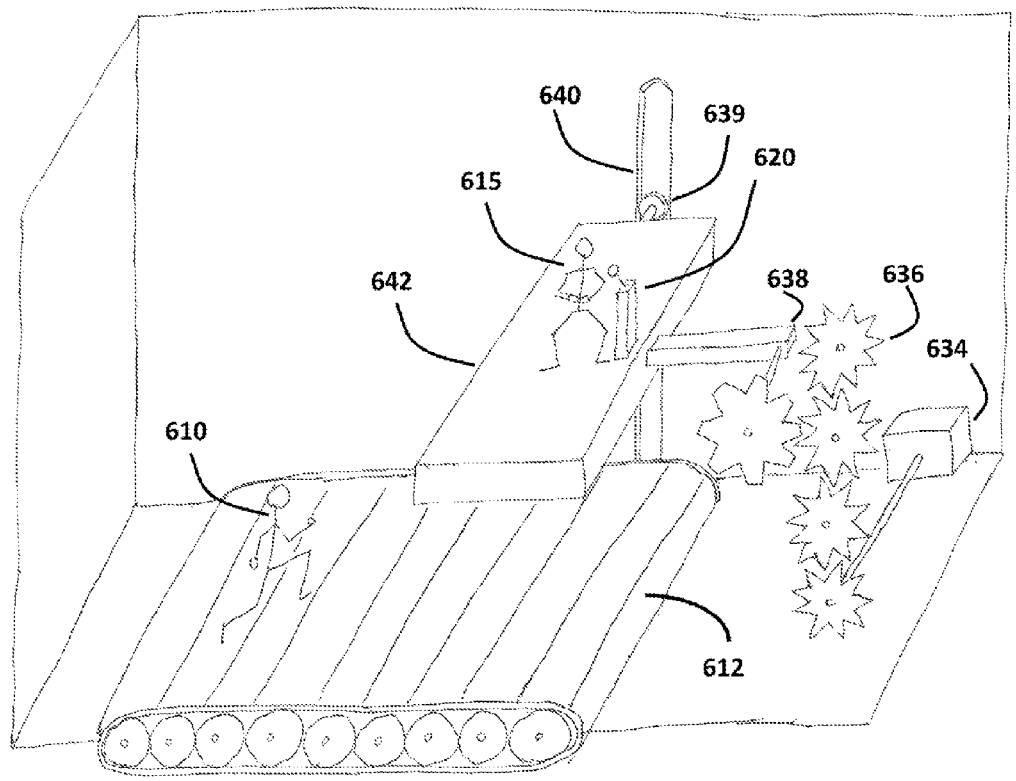
FIG. 6 illustrates a room with a moving walkway spanning its width and length beneath platform which may be raised and lowered by a system of motors, gears, guides, and pulleys, located in the walls and adjacent rooms.
Figure 7:
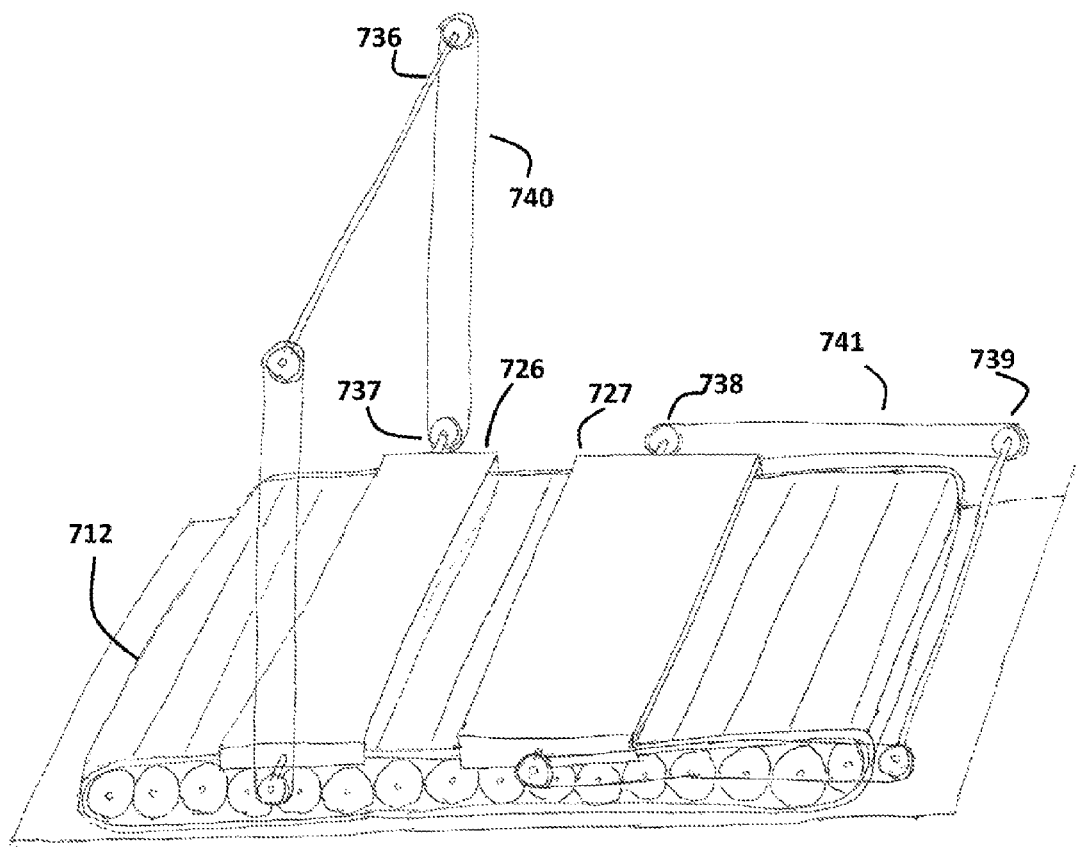
FIG. 7 illustrates a room with a moving walkway spanning its width and length, beneath a plurality of platforms moving in various directions.
Figure 8:
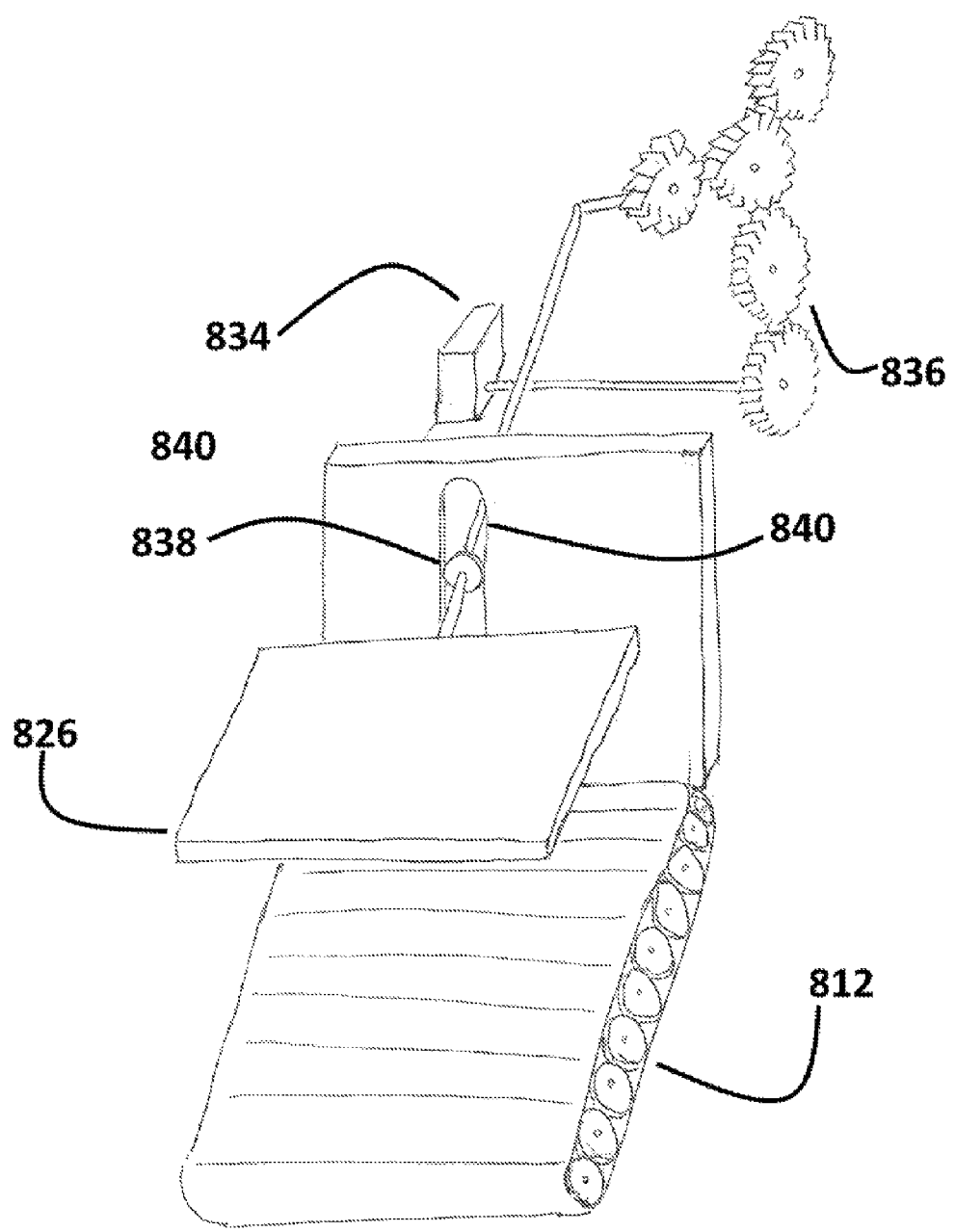
FIG. 8 illustrates a cross-sectional orthogonal view of a room containing a platform which may raise and lower to start and stop the moving walkway.
Figure 9:
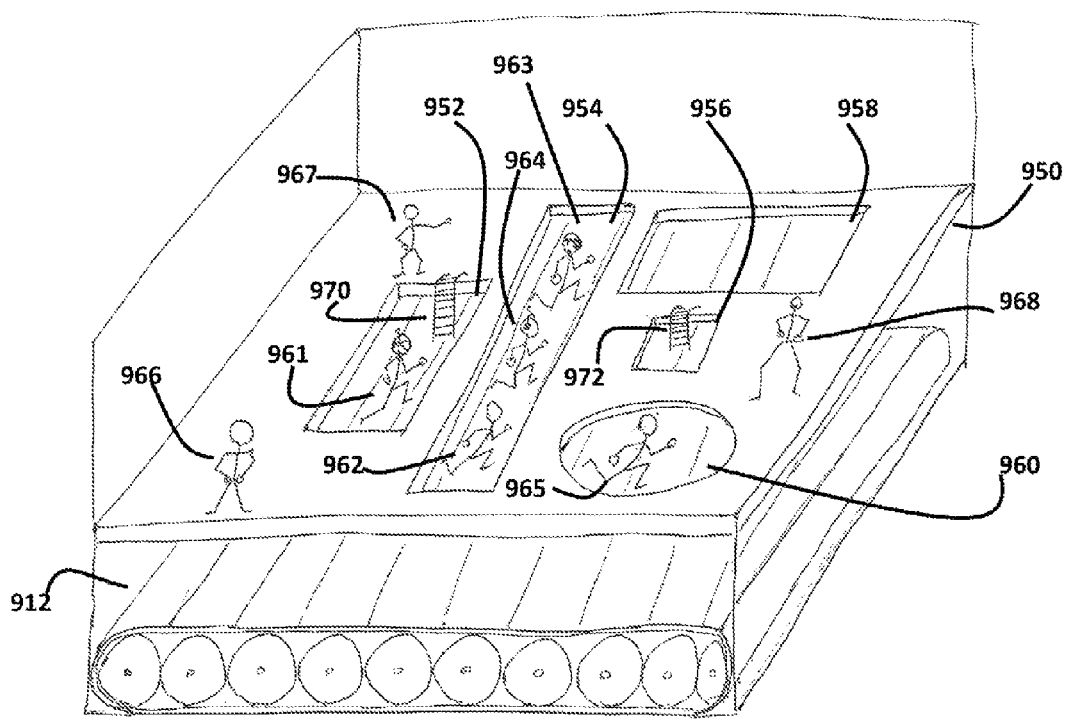
FIG. 9 illustrates room with a moving walkway spanning its entire length and width, and a floor at an elevation above said moving walkway, the floor containing a plurality of holes, large enough for users to enter.
Figure 10:
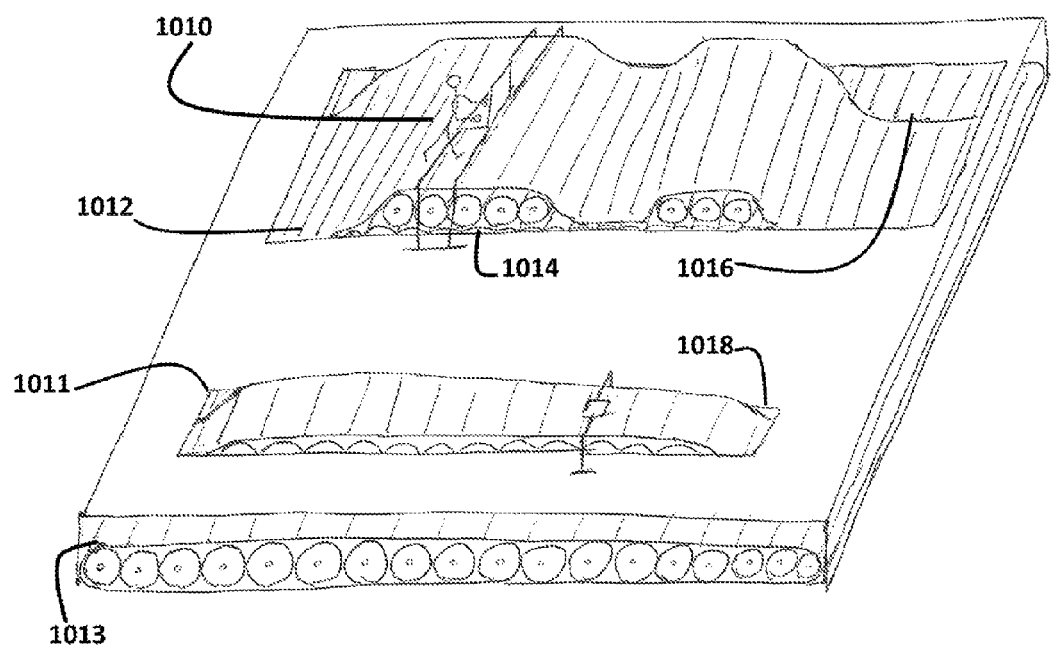
FIG. 10 illustrates room with a moving walkway spanning its entire length and width, with rollers stacked beneath select widths of moving walkways with more pallets than adjacent portions of moving walkways, placed directly within holes in a floor located above all portions of the moving walkway which are not directly beneath said holes.
Figure 11:
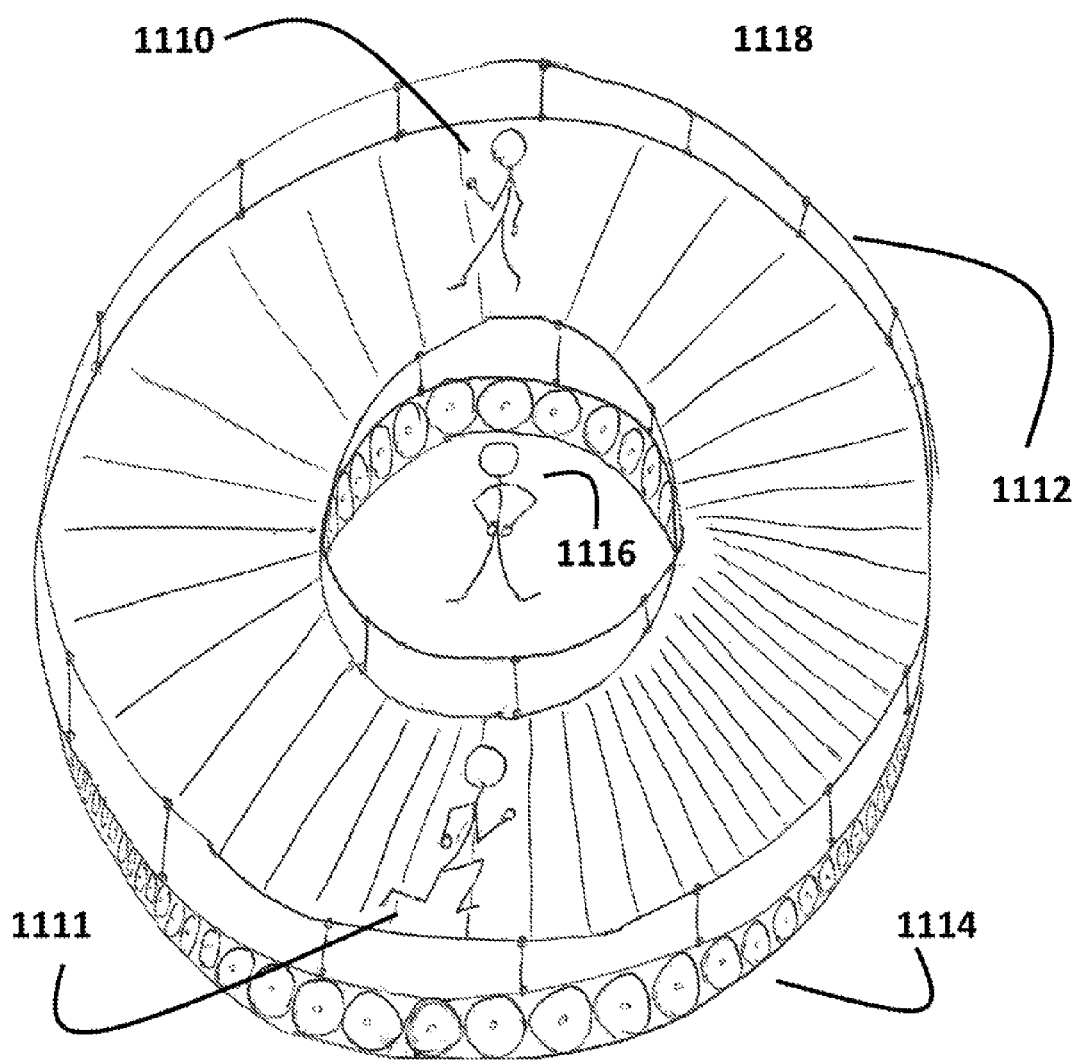
FIG. 11 illustrates an area with a circular treadmill, guided by a system of rollers wherein said treadmill is in use by a plurality of users.
Figure 12:
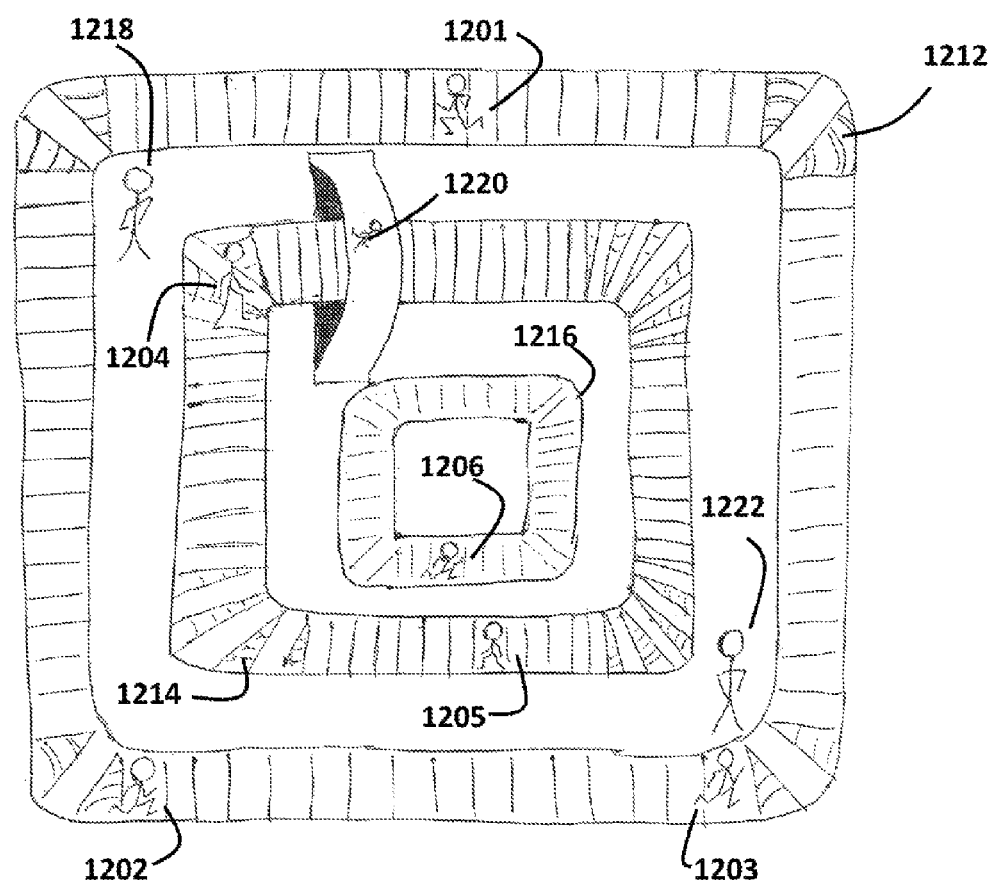
FIG. 12 illustrates an area with a plurality of users on a plurality of moving walkways, arranged in a concentric pattern, while a plurality of observers stands outside of the moving walkways on land in between or above said moving walkways.
Figure 13:
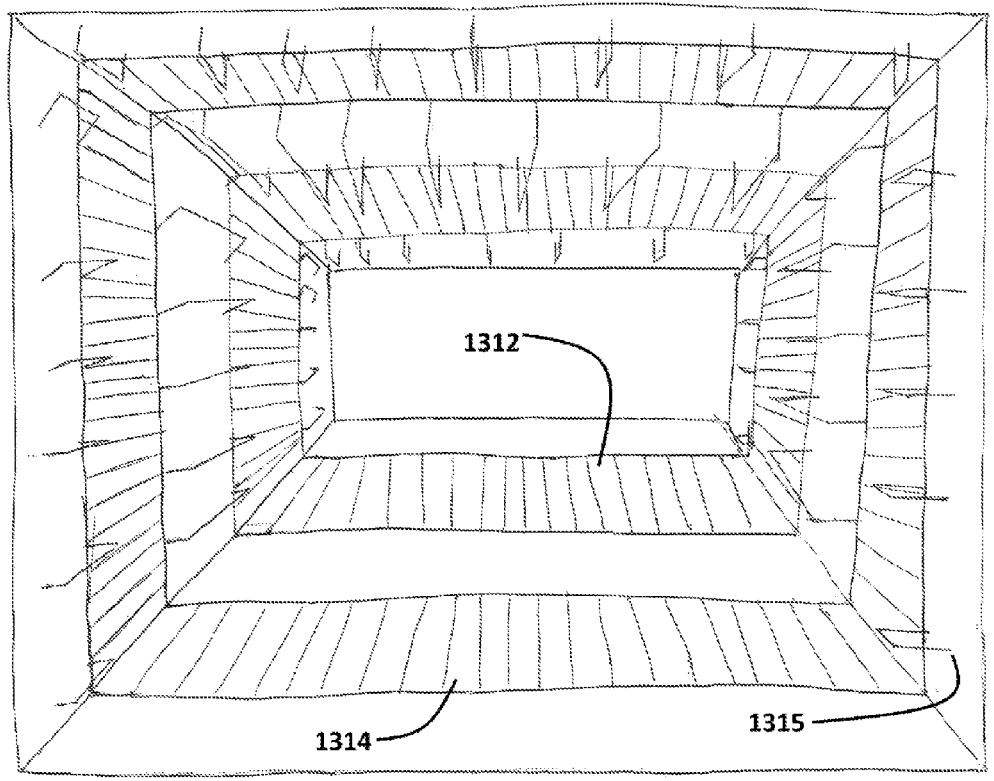
FIG. 13 illustrates a room with a plurality of moving walkways revolving the width of the room from the floor to the ceiling, and staggered handlebars for a user to traverse the room in a direction the same as or opposite of the moving walkway.
Figure 14:
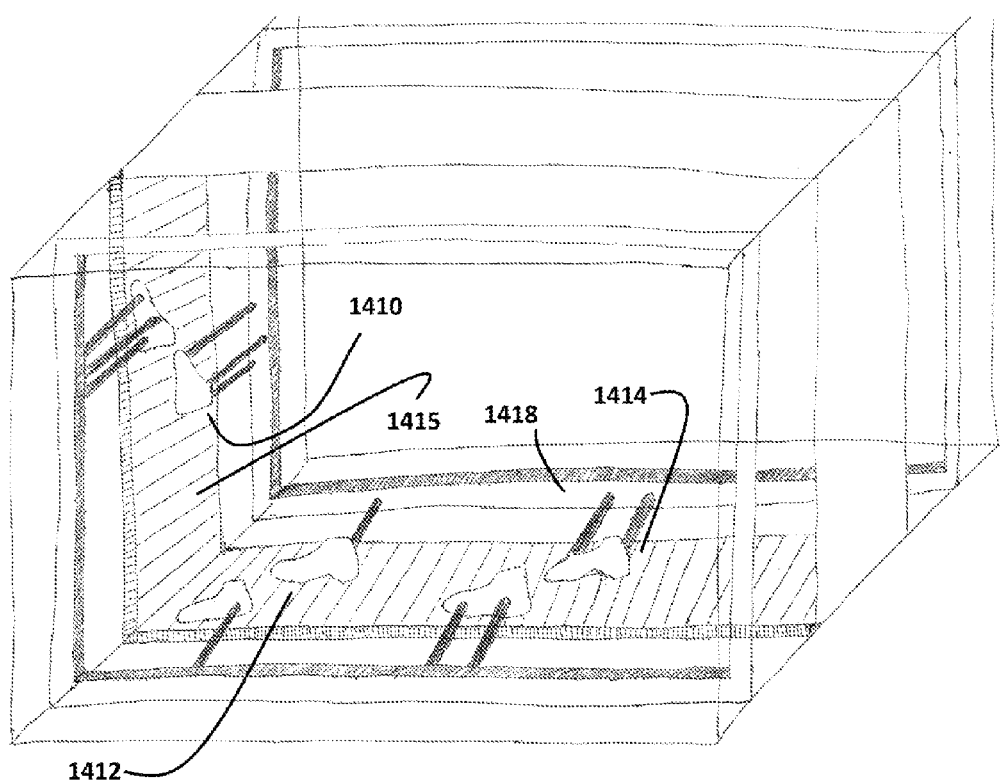
FIG. 14 illustrates a room with a plurality of users traversing a moving walkway revolving the width of the room from the floor to the ceiling, said room containing floor guides with shoe attachments to aid the user in revolving the room.

This disclosure relates to rooms and areas designed to stimulate education, work, meditation, or entertainment while including one or more movement devices. These movement devices may include but are not limited to a treadmill spanning the entire floor of a room, a treadmill spanning the width of the room, a treadmill spanning the length and width of a room with one or more moving platforms above said treadmill, a group of elliptical machines in a classroom setting, a group of treadmills with moving desks imbedded in a work setting. In some embodiments one or more sensor relays may collect information from users and send said information through one or more devices which may translate or analyze said information before sending it to a decision maker or a movement device to aid in the users learning or movement.

In this disclosure the term 'sensor relay' refers to an apparatus which may be composed of any or any combination of devices including but not limited to: sensors (including an audio sensor, a visual sensor, a tactile sensor, a gyroscope, an accelerometer, proximity device, or a magnetometer) and relays for sending information such as sensory information or positional information. These may include input or output relays, or any combination therein which may send or receive one or more signal from the user, an observer, any extension of the user, computer processor or any other sensor relay.

The computer processor is a device which may receive, process, store, or transmit information. The sensor relay may send a signal to the computer processor, another sensor relay, an output device, or a movement device. The computer processor may receive the information from a variety of sources including but not limited to the sensor relays, movement devices, output devices, media devices or any combination thereof. The computer processor may then process the information in a number of different ways including but not limited to analyzing it comparatively against a set point or combination of set points.

Set points are permanent or adjustable values of attributes that may be predefined by individuals, including but not limited to a user, an observer, or a manufacturer. The computer processor may send a signal or combination of signals to a variety of devices including but not limited to other computer processors, sensor relays, output devices, movement device, or media devices.

The output device is a device that may include a computer processor which receives information from a source, including but not limited to a sensor relay or computer processor. The output device may then convert or convey this information, or any combination therein to the user or an observer through any of multiple means, including but not limited to headphones, speakers, a visual monitor or by controlling a movement device. The output device may be or may include a media device.

The media device may have a processor which receives and outputs information as media information. Media information may include learning material (including but not limited to either audio or visual lectures, quizzes, or books) entertainment material (including but not limited to movies, music, or video games), or simulation material (including but not limited to computing material, material directly related to the users movement for physiotherapy, or exercise assistance material). The media device may adjust its rate of output of media information if directed to do so by its processor. The media device's processor may receive information from a variety of sources including but not limited to users, observers, computer processors, output devices, or sensor relays.

Any signal sent from a sensor relay, computer processor, output device or media device to another can be sent by means including but not limited to wired means (including but not limited to coaxial, vga, hdmi, component, composite, fiber optic, or dvi cables) or wireless means (including but not limited to bluetooth, wifi, or infrared or other electromagnetic waves). Any signal sent from an output device to either a user, observer, any extension of the user or any sensor relay may be sent via means including but not limited to visual, audio, or tactile means.

In some embodiments where it receives signals, the sensor relay may include audio sensors that can receive input from the user or an observer related to sounds that they make, purposely or otherwise. The audio sensor may be comprised of a variety of audio devices including but not limited to microphones or vibration monitors.

In other embodiments the sensor relay may include visual sensors that can detect movement including but not limited to movement of the user's body, any body parts, extensions of the user's body, or eyes (including but not limited to pupil dilation, eye-crossing, eye wiggles, rapid-eye movement, or normal eye movement). The visual sensor may be comprised of a variety of video devices including but not limited to cameras or optical sensors.

In other embodiments the sensor relay may include tactile sensors which may sense contact (including but not limited to touching, depressing or hitting) or changes in contact (including but not limited to grip modulation, sweating, altered breathing, altered pulse, shaking or swiping) that any part of the user's body, observer's body, or extensions of their bodies (including but not limited to clothes, gloves, or any object directly connected to them) or any combination thereof makes with the sensor or any extension connected to the sensor via wired or wireless means.

In other embodiments the sensor relay may include a gyroscope which may detect changes in the location of one body part or extension of body part in relation to another or from its original position, such as but not limited to those indicating alterations in balance, angular velocity, angular momentum, spin, inertia, or torque. In other embodiments the sensor relay may include an accelerometer which may detect the user's average speed, velocity, or any changes therein. In other embodiments the sensor relay may include a magnetometer which may detect changes in magnetization or proximity of a magnetized object connected to the user or any extension of the user.

A movement device may include but is not limited to devices used to facilitate movement or exercise such as a treadmill, bicycle, cable-row, or elliptical. In certain embodiments of the disclosure users, observers, sensor relays or computer processors may direct the movement device to alter its settings, including but not limited to its velocity, resistance, incline, or pressure.

In certain embodiments of the disclosure one or more users, 110, on one or more movement devices, 112, may receive feedback from sensor relays, 114, directed to an output device. An observer, 115, may be present. In some variations this sensor relay may send feedback including but not limited to information concerning the users balance or speed, to an output device, such as a user headset, 116, while the user is reviewing learning content on a pair of virtual glasses, 118. In other variations the sensor relay may send a signal to the movement device or the glasses to pause or slow movement or content respectively.

In other embodiments of the disclosure a plurality of users, 210, 211, on a plurality of moving devices, 212, 213, may receive feedback from one or more sensor relays, 214, 215, 216 transmitting signals to one or more output devices, 220, 221, 222. In some variations a signal may be sent by one or more sensor relays, monitoring a user working at a standing desk, to an observer, 225, with an output device that receives said signal. That signal may concern an indication that the user is falling asleep as detected by cameras in the user's glasses detecting a slower writing speed than usual. The observer may then make a decision to press a button on their own sensor relay stopping that user's movement. In another variation a signal may be sent by both users' sensor relays on their legs, recording average speed, to the output device of one user, in some instances a computer terminal, on which the user can see that they are lagging behind the other user, and may decide to slow their typing speed and focus on movement, to match or outpace a rival user.

In another embodiment of the disclosure a user, 310, utilizing a movement device, 312, (in this case a circular treadmill) may operate a media device, 323, (in this case a computer) which moves in harmony with their own movements. This harmonious movement may be accomplished by a variety of methods, including but not limited to a user with a harness, 324, which is attached to both the user's waist and a set of rods, which cause the desk of the computer to move in response to the user's movements, as the user walks along a track, 325, on top of the circular treadmill. In certain embodiments this device may include supports, 326, for handle bars, 327, which may be used for a variety of purposes, including but not limited to guiding the user as they traverse the track through the use of their body, hands, or straps attached to the user's body, or any part of their body and the handle bars.

Other methods of accomplishing this harmonious movement may involve a media device with a visual sensor relay in the form of cameras, which detects the users hand movement, and sends a signal to a motor, to slide the keyboard desk in and out accordingly, so that the user may type fluidly while still moving slightly.

Another embodiment of the disclosure may involve a room wherein a treadmill, 412, spans the entire floor. This may have uses including but not limited to: group training exercises, a classroom where a monitor on the front wall displays a lecture to students moving at a slow walking pace on the treadmill, or a brainstorming room allowing users to walk and engage in comfortable discourse.

Another embodiment of the disclosure may involve a room wherein a treadmill, 512, spans the entire width of the room. This may allow space for stationary platforms, 530, 531, which may be used in some variations for user rest areas, or an area for an observer to stand while giving the users a seminar.

Another embodiment of the disclosure may relate to a room with a user, 610, moving on a treadmill, 612 spanning the room's width, portions of said treadmill being beneath a platform which spans part of the same area. In some variations this platform may be raised and lowered at the behest of an observer, 615, in some instances it may be in response to the observer depressing of a tactile sensor relay, 620. The platform may be moved by a system containing any number of motors, 634, gears, 636, guides, 638, 639, and pulleys, 640. In other variations this platform, 642, may be stationary and slightly above the treadmill, and accessible ladder. In other variations the treadmill may stop once the added weight of the platform is loaded on to it. Then the treadmill may start up again once the platform raises and the observer is safely above the treadmill.

Other embodiments may involve a moving walkway, 712, spanning the length and width of the room, beneath a plurality platforms, moving in various directions, including vertical, 726, and horizontal, 727. These platforms may be guided by a system of motors, gears, guides, 738, 739, and pulleys, 740, 741 moving an axis connected to the platform in a desired direction. This room may be used for a variety of purposes, including but not limited to a simulation room, game room, or obstacle course.

Certain embodiments may contain a treadmill, 812 spanning its width and length, said walkway being beneath a platform, 826 which spans part of the same area. In some variations this platform may be raised and lowered by a system of motors, 834, gears, 836, guides, 838, 839, and pulleys, 840, located in the walls and adjacent rooms. In some variations this platform may raise to nearly the height of the ceiling automatically.

Other embodiments may involve a room comprising a moving walkway, 912, spanning its entire length and width, and a floor, 950 at an elevation above said moving walkway, the floor containing a plurality of holes, 952, 954, 956, 958, 960, large enough for a plurality of users, 961, 962, 963, 964, 965 to enter while being monitored by one or more observers, 966, 967, 968. Variations of this embodiment may involve holes of various sizes, for different user arrangements. Other variations may involve holes with ladders, 970, 972, for users to access said holes.

In other embodiments users, 1010, may move on raised portions, 1011, 1012 of a treadmill, 1013, spanning the room's length and width, with rollers, 1014, stacked beneath select widths of the treadmill, fitting between holes, 1016, 1018, in a floor above all unraised portions of said treadmill. In some variations raised portions of the treadmill may be level with the elevation of the floor, while in other variations it may be lower or higher. These variations may allow for advantages including but not limited to safety of dismounting, ease of building, and aesthetics.

Another embodiment of this disclosure may involve an area with a plurality of users, 1110, 1111, on a circular treadmill, 1112, guided by a system of rollers, 1114, as an observer, 1116, watches. In some variations users may be assisted in movement and prevented from falling out by means including but not limited to guide rails, 1118.

Other embodiments may involve a plurality of users, 1201, 1202, 1203, 1204, 1205, 1206, on a plurality of moving walkways, 1212, 1214, 1216 arranged in a concentric pattern, while a plurality of observers, 1218, 1220, 1222 stands outside of the moving walkways, on land in between or above said moving walkways. In certain variations the users or observers would be able to control the speed of certain moving platforms.

Another embodiment may involve a plurality of moving walkways, 1312, 1314 revolving the width of the room from the floor to the ceiling, and staggered handlebars, 1315 for a user to traverse the room in a direction the same as or opposite of the moving walkway.

Yet another embodiment may involve a room with a plurality of users, 1410, 1412, 1414, traversing a moving walkway, 1415, revolving the width of the room from the floor to the ceiling, said room containing floor guides with shoe attachments, 1418, to aid the user in revolving the room. In some variations these shoe attachments may be elastic to help the user walk around without falling from the floor guides. In other variations the users' walking may be further supplemented in their endeavors to walk the ceiling by magnetic boots, which allow a user to step on a moving walkway, where the floor pallets are metal.

Another embodiment of this disclosure may be a method for teaching students utilizing one or more treadmills or moving walkways to present educational material to one or more students while said students are in motion. In some variations, the treadmill or moving walkway may span the majority of the floor of the classroom. In other variations, the classroom may have one or more treadmills or moving walkways assigned to individual students. In other variations, the students may be fitted with sensor relays that monitor and relay information on one or more attributes related to the user's movement such as pulse, speed, or fatigue.

In another embodiment, users may be fitted with headsets or displays at their individual workstations. Said headsets or displays may be used to present learning material. An advantage of the described teaching method may be utilizing the effects of movement to increase concentration, focus, and attention span. Another advantage of the described teaching method may to promote regular exercise and multitasking.

It is understood that the various preferred embodiments are shown and described above to illustrate different possible features of the disclosure and the varying ways in which these features may be combined. Apart from combining the different features of the above embodiments in varying ways, other modifications are also considered to be within the scope of the disclosure.

The invention is not intended to be limited to the preferred embodiments described above, but rather is intended to be limited only by the claims set out below. Thus, the invention encompasses all alternate embodiments that fall literally or equivalently within the scope of these claims.

Having thus described our invention, we claim:

1. A system for teaching while performing movement exercises in a dedicated area, the area comprising a plurality of devices including:
   one or more sensor relay devices having at least one sensor;
   any number of output devices; one or more movement devices;
   and one or more computer processors that:
   receive a relay signal from any of the one or more sensor relays, detecting information related to the user;
   analyze the detected information against one or more manufacturer defined, observer defined, or user defined set points;
   and either
   send a signal to any of the output devices instructing the decision maker with feedback related to one or more sensor detected user performance related activities measured against one or more set points;
   or
   send a signal to any of the movement devices controlling said movement devices based on said analysis.

2. The system of claim 1, further comprising one or more communication means for enabling communication between the plurality of devices, wherein said plurality of devices are:
   movement devices,
   output devices,
   media devices,
   or
   computer devices,
   communicating directly with each other independent of the system's sensor relays.

3. The system of claim 2, wherein the communication means is a wired communication means.

4. The system of claim 2, wherein the communication means is a wireless communication means.

5. The system of claim 1, wherein the dedicated area comprises one or more physical assistance means for assisting a user while walking on the movement device.

6. The system of claim 5, wherein the physical assistance means is a handle bar configured on peripheral walls/ceiling of the dedicated area.

7. The system of claim 1, wherein the plurality of devices comprises one or more moveable platform devices.

8. The system of claim 7, wherein the platform devices are movable in a vertical, horizontal, up and down direction.

9. The system of claim 1, wherein the movement device is a circular treadmill.

10. The system of claim 1, wherein the movement device is a walkway.

11. The system of claim 1, wherein the relay signal is a signal related to a user's activity and sensed by the sensor of the sensor relay device.

12. The system of claim 1 wherein the sensor relay sends signal to one or more computer processors for controlling one or more movement devices.

13. The system of claim 1 wherein the sensor relay sends signal to one or more computer processors for controlling one or more output devices.

14. The system of claim 1, wherein the output device is a headset.

15. The system of claim 1, wherein the output device is a media device.

16. A method of teaching comprising the steps of:
   having one or more students in motion through the use of one or more movement devices;
   presenting the student with educational material while the student is in motion;
   said student assisted through the use of one or more sensor relays that may detect and relay signals, conveying information related to one or more sensor detected user performance related activities measured against one or more set points, controlling:
   one or more output devices,
   one or more movement devices,
   or
   one or more computer processors;
   and the control of the devices or processors altering based on said sensor relay relayed information that is analyzed by a processor as measured against one or more manufacturer defined, observer defined, or user defined set points.

17. A method of teaching according to claim 16 further comprising the step of having the student interact with educational material while moving on a circular treadmill, said educational material being presented on a virtual reality headset.

18. A method of teaching according to claim 16 further comprising the step of having one or more students interact with each other or with one or more teachers or any combination of students and teachers.

19. A system for teaching while performing movement exercises in a dedicated area, the area comprising a plurality of devices including:
   one or more sensor relay devices having at least one sensor;
   any number of output devices; one or more of movement devices;
   and one or more computer processors that:
   receive a relay signal from any of the one or more sensor relays, detecting information related to the user;
   analyze the detected information against any number of user defined set points;
   and either
   send a signal to any of the output devices instructing the decision maker with feedback related to one or more sensor detected user performance related activities measured against one or more set points;
   or
   send a signal to any of the movement devices controlling said movement devices based on said analysis;
   wherein the information detected from the user relates to their performance on a movement device, an output device or a computer processor.

20. The system of claim 19, wherein one of the user's output devices is a virtual reality headset which adjusts a movement device or user content based on performance.

* * * * *